US012678758B2

(12) United States Patent
Rychecky et al.

(10) Patent No.: US 12,678,758 B2
(45) Date of Patent: Jul. 14, 2026

(54) DEVICE AND METHOD FOR PREPARATION OF LIQUID MARBLES

(71) Applicant: VYSOKA SKOLA CHEMICKO-TECHNOLOGICKA V PRAZE, Prague (CZ)

(72) Inventors: Ondrej Rychecky, Brasy (CZ); Frantisek Stepanek, Prague (CZ); Martin Krov, Stare Hodejovice (CZ)

(73) Assignee: VYSOKA SKOLA CHEMICKO-TECHNOLOGICKA V PRAZE, Prague (CZ)

( * ) Notice: Subject to any disclaimer, the term of this patent is extended or adjusted under 35 U.S.C. 154(b) by 999 days.

(21) Appl. No.: 17/800,019

(22) PCT Filed: Feb. 17, 2021

(86) PCT No.: PCT/CZ2021/050019
§ 371 (c)(1),
(2) Date: Aug. 16, 2022

(87) PCT Pub. No.: WO2021/164797
PCT Pub. Date: Aug. 26, 2021

(65) Prior Publication Data
US 2023/0074000 A1 Mar. 9, 2023

(30) Foreign Application Priority Data
Feb. 18, 2020 (CZ) .................................. CZ2020-84

(51) Int. Cl.
*B01J 13/04* (2006.01)
*C12N 5/00* (2006.01)

(52) U.S. Cl.
CPC ............ *B01J 13/04* (2013.01); *C12N 5/0075* (2013.01); *C12N 2531/00* (2013.01)

(58) Field of Classification Search
CPC ....................................................... B01J 13/04
See application file for complete search history.

(56) References Cited

U.S. PATENT DOCUMENTS 4,767,630 A * 8/1988 Silver ..................... A23L 19/05
426/639
5,629,187 A * 5/1997 Ors ........................... B01J 2/08
426/11
6,251,466 B1 6/2001 Mcguire et al.

FOREIGN PATENT DOCUMENTS

JP H02169026 A 6/1990

OTHER PUBLICATIONS

Rychecký, Ondřej et al., "Spheroid cultivation of HT-29 carcinoma cell line in liquid marbles", Chemick Zvesti—Chemical Papers, Dec. 5, 2016 Veda, Bratislava, SK—ISSN 0366-6352, vol. 71, Nr:6, pp. 1055-1063, http://dx.doi.org/10.1007/s11696-016-0026-2, retrieved Aug. 16, 2022.

(Continued)

*Primary Examiner* — Mark L Shibuya
(74) *Attorney, Agent, or Firm* — Notaro, Michalos & Zaccaria P.C.

(57) ABSTRACT

A device for preparation of liquid marbles that has a belt conveyor for carrying a layer of solid particles, the belt conveyor being provided, successively in the direction of movement of the belt with at least one solids dispenser with a reservoir for solid particles, at least one liquid dispenser with a reservoir for liquid, and a separator for separating the prepared liquid marbles from solid particles, is disclosed.

19 Claims, 1 Drawing Sheet

(56)     References Cited

OTHER PUBLICATIONS

Roxana-Elena Avrămescu, et al., "Liquid Marbles: From Industrial to Medical Applications", Molecules Springer Verlag, Berlin, DE—ISSN 1433-1373 , vol. 23, Nr:5, pp. 1120, http://dx.doi.org/10.3390/molecules23051120, retrieved Aug. 16, 2022.

Bhosale Prasad et al., "Mechanically robust nanoparticle stabilized transparent liquid marbles", Applied Physics Letters, 20080725 American Institute of Physics, 2 Huntington Quadrangle, Melville, NY 11747—ISSN 0003-6951, vol. 93, Nr:3, pp. 34109-34109-3, http://dx.doi.org/10.1063/1.2959853, retrieved Aug. 16, 2022.

International Search Report and Written Opinion for corresponding PCT application No. PCT/CZ2021/050019, mailed Apr. 23, 2021.

* cited by examiner

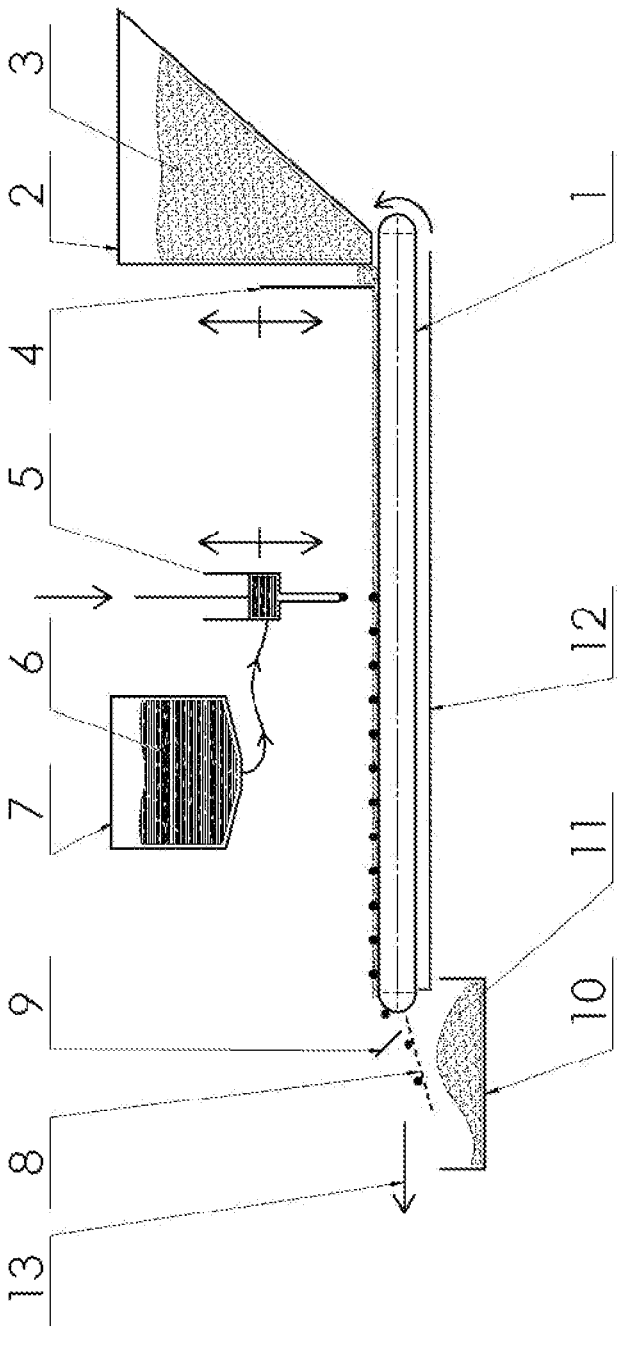

DEVICE AND METHOD FOR PREPARATION OF LIQUID MARBLES

FIELD OF ART

The present invention relates to a device and a method for preparation of liquid marbles.

BACKGROUND ART

A liquid marble is a droplet of liquid wrapped by solid particles. Most commonly, a liquid marble is a droplet of water wrapped by hydrophobic particles; less commonly, inversed liquid marbles are provided, for example a droplet of oil wrapped by oleophobic particles. The liquid phase (e.g., water or oil) usually contains a dissolved active ingredient. When a liquid marble is produced, the active ingredient is encapsulated in the liquid marble. Liquid marbles may prevent the deterioration of the encapsulated ingredient. Dissolution of an active ingredient may increase its bioavailability. Changes in the composition of the liquid marbles may affect the release rate of the encapsulated ingredients, hence liquid marbles are used in cosmetic [McHale, G., & Newton, M. I. (2011). Liquid marbles: principles and applications. *Soft Matter,* 7(12), 5473-5481] or potentially in pharmaceutical industry [Janská P., Rychecký O., Zadražil A., Štěpánek F., Čejková J. (2019): Liquid oil marbles: increasing the bio-availability of poorly water-soluble drugs. *Journal of Pharmaceutical Sciences,* 108(6), 2136-2142]. Further uses of liquid marbles include cultivation of tumor cells to form a three-dimensional structure [Rychecký O., Majerská M., Kral V., Štěpánek F., Čejková J., "Spheroid cultivation of HT-29 carcinoma cell line in liquid marbles", *Chem. Pap.* 71, 1055-1063 (2017)].

The most common preparation of liquid marbles on a laboratory scale is batch preparation on a Petri dish with a bed of solid particles, wherein after dripping the liquid the formed droplet of the liquid is coated with solid particles due to movement of the dish. Only a few individual liquid marbles are prepared in each batch. Translating such preparation process to an industrial scale would present many technical problems [Avrămescu R.-E., Ghica M.-V., Dinu-Pirvu C., Udeanu D., Popa L. (2018): Liquid marbles: From industrial to medical applications. *Molecules.* 23(5): p. 1120]. Another method of preparation of liquid marbles consists of dripping water onto a stationary bed of hydrophobic solid particles, but even so the droplet of water is coated. However, this phenomenon is described only for systems comprising water and very hydrophobic solid particles (contact angle greater than 150°). The disadvantage is that the solid particles must not be compressed into a consolidated layer, because in this case the self-coating of the droplet would not occur. Therefore, each liquid marble must be prepared on a freshly poured bed of solids [Bhosale P. S., Panchagnula M. V., Stretz H. A. (2008): Mechanically robust nanoparticle stabilized transparent liquid marbles. *Applied Physics Letters.* 93(3): p. 034109]. A similar approach utilizes a particle bed on top of a rotating disc, which forces the droplet to roll to the edge, vacating the impact area and covering the droplet in the process. While this method can be operated semi-continuously, the achieved production rate was only 1 liquid marble per 7.5 s and the particle bed was renewed manually [Lekshmi, B. S., et al., *Simple and Continuous Fabrication of Janus Liquid Marbles with Tunable Particle Coverage Based on Controlled Droplet Impact.* Langmuir, 2020. 36(50): p. 15396-15402]. Another possibility for preparation of liquid marbles is a method using evaporation of liquid from parental marbles and formation of daughter marbles. This method can prepare small marbles, but because the liquid must evaporate from the parental marbles, the temperature must be raised, which can lead to thermal destruction of the encapsulated active ingredients [Bhosale P. S. a Panchagnula M. V. (2012): Sweating liquid micro-marbles: dropwise condensation on hydrophobic nanoparticulate materials. *Langmuir.* 28(42): p. 14860-14866]. A recently described method ispreparation of liquid marbles using electronegatively charged particles. The dripping liquid is oppositely charged than the solid particles below it, and so the particles adhere to the forming droplet. The disadvantages of this procedure are problematic control of the thickness of the solid shell of the marbles, and further processing of the electro-charged particles which adhere to further components of the production device [Ireland P. M., Thomas C. A., Lobel B. T., Webber G. B., Fujii S., Wanless E. J. (2018): An electrostatic method for manufacturing liquid marbles and particle-stabilized aggregates. *Frontiers in chemistry.* 6].

The technologies described above make it possible to produce liquid marbles only in small quantities corresponding to laboratory scale, but it is problematic or impossible to convert them to an industrial scale. Current preparation technologies also require a great deal of manual skill on the part of the operator, which increases the costs of producing liquid marbles, and therefore the technologies are unsuitable for industrial use.

Commercially available encapsulators cannot prepare liquid marbles because the liquid is usually sprayed into an air stream (spray dryer) or into another liquid (preparation of core-shell particles). The size of the thus prepared particles is quite often smaller than the size required for liquid marbles, because as the particle diameter decreases, the weight ratio of liquid to powder decreases due to the volume to surface ratio of a sphere.

The aim of the present invention is to provide a device which enables to produce liquid marbles of a precisely defined composition and size, on an industrial scale and in desired amounts, in a continuous mode. To do this, it is necessary to ensure accurate dosing of the liquid, and at the same time movement of the particles so that each droplet remains separated on the bed of solid particles and does not merge with another droplet. Furthermore, it is necessary to ensure the coating of the remaining part of the droplet so that it does not come into contact with another droplet. Yet furthermore, it is necessary to ensure the separation of the formed liquid marbles from the excess solid particles for possible recycling of solid particles.

DISCLOSURE OF THE INVENTION

Object of the present invention is a device for preparation of liquid marbles which comprises a belt conveyor for carrying a layer of solid particles, said conveyor being provided, successively in the direction of movement of the belt, with at least one solids dispenser with a reservoir for solid particles, at least one liquid dispenser with a reservoir for liquid, and a separator for separating the prepared liquid marbles from solid particles.

The solids dispenser dispenses a predetermined amount of solid particles onto the belt conveyor, preferably in an even layer (i.e., a layer of even height). Thus, the device may advantageously comprise means for adjusting the height of the layer of solid particles, said means being located behind the solids dispenser. The means for adjusting the height of the layer of solid particles may be for example a stop which may be height-adjustable for setting various heights of the layer of solid particles. The height of the layer is determined by the height of the gap between the belt conveyor belt and the stop. Effective height of the layer of solid particles is typically from 1 mm to 20 mm, in some embodiments from 1 mm to 4 mm, depending on the type of liquid marbles produced. The means for adjusting the height of the layer of solid particles also ensure that the layer of solid particles is evenly distributed over the belt or that a layer with a defined shape is prepared, so that lower consumption of solid particles in the process can be achieved. The stop can be, for example, a flat plate or protruding elements forming a precisely defined layer, the shapes preferred for the stop being triangular, trapezoidal, rectangular or circular.

In preferred embodiments, the solids dispenser with the container for solids may be in the shape of a truncated cone (a hopper), a bevelled block, a cylinder, or a cube.

The solids dispenser with the container for solids may preferably be equipped with an agitator, a rotating disk with blades, or a vibrating wall, which prevents the formation of a arching inside the solids dispenser.

The liquid dispenser may preferably comprise at least one reservoir for liquid and/or at least one pump and/or at least one outlet. The pump for accurate liquid dosing can be of the batch type (e.g. syringe pump, syringe, piston in a heated block, pneumatic pump, linear pump), continuous type (e.g. peristaltic pump, centrifugal pump, gear pump, spindle pump, single-channel or multiple-channel dispense solenoid valve, diaphragm pump, vane pump). Alternatively, the liquid dispenser may comprise a system utilizing hydrostatic pressure or compressed gas pressure. The flow and dosing of the liquid should be stable to avoid the formation of drops of varying sizes. Continuous operation is also possible using a set of two or more batch systems, wherein one or more batch systems are dispensing and other batch systems are being prepared for dispensing. When the liquid in one system is used up, another system is turned on. The size of the droplet is usually controlled by adjusting the dispenser and using a suitable material and shape of the dispenser outlet, as well as the properties of the liquid, especially its viscosity, surface tension, and also the temperature at which the liquid is dispensed.

The liquid dispenser and/or its outlet may preferably be height-adjustable. The height from which the droplet falls into the layer of solid particles can affect the size of the liquid marble and its other parameters.

The liquid dispenser may preferably be provided with a system for maintaining the liquid temperature, which may comprise heating or cooling elements (e.g. resistance heating, Peltier element, circulating heat transfer medium), one or more temperature sensors and a control and/or evaluation unit.

The outlet of the liquid dispenser may be, for example, a hollow capillary, for example with an inner diameter of 0.05 to 2.5 mm, or a set thereof, then the droplet size is affected by the capillary material and diameter, geometry and cross-section, and liquid properties. In some embodiments, the liquid dispenser outlet may be a needle with an inner diameter of 0.1 mm to 0.9 mm (corresponding to 20 to 30 G needles) with a Luer-lock or Luer-slip system with a straight or bevelled tip. The volume of droplets from said needles typically ranges from 0.9 mm$^3$ to 14 mm$^3$ and the dripping rate is in the range of 1 to 100 Hz, depending on the volume of the droplets and the liquid flow, ideally 10 to 20 Hz.

The liquid dispenser may further be provided with a system for accurate and rapid droplet formation which vibrates regularly in contact with the dispenser. Such systems may include, for example, a diaphragm compressed by a regularly moving piston (e.g. a piston from a loudspeaker), a piezoelectric transducer acting on a liquid, a diaphragm compressed by a solenoid with a spring, a device producing an air flow along the dispenser needle, a device causing mechanical vibration of the needle in the longitudinal or transverse direction. By setting the system correctly, the droplet size can be reduced to a volume of 0.15 mm$^3$ and the dripping frequency can be increased up to 150 Hz.

The liquid dispenser may further be provided with a drip accuracy sensing system, which may comprise a sensor sensing the number of drops per time unit and their size, and a control and/or evaluation unit. This system can also be connected to a liquid dispenser control unit to form a feedback loop.

The belt conveyor carries a layer of solid particles and moves continuously with it, at the same time droplets of liquid from one or more liquid dispensers fall onto this layer. In preferred embodiments, the belt conveyor may be provided with multiple solids dispensers and/or multiple liquid dispensers. Multiple solids dispensers allow defined mixing of different types of solid particles as needed. In some embodiments, one or more solids dispensers are located at the beginning of the belt conveyor (upstream of the liquid dispenser(s)), and one or more solids dispensers are located downstream of the liquid dispenser(s). Multiple liquid dispensers allow to increase the capacity of the device, or to prepare a defined mixture of liquid marbles. The belt conveyor may also be provided at one or more locations with a rake for rearranging the particles during the production of the liquid marbles. The rake is preferably height- and direction-adjustable.

The surface of the belt conveyor belt may preferably be made of a material which does not adhere to the solid particles used or to the liquid used, and which does not impart any electrostatic charge to the resulting particles. Such material is typically a material selected from the group consisting of teflonglass fabrics, teflon (polytetrafluoroethylene), silicone, metal, polyvinyl chloride, polyurethane, polyethylene, thermoplastic elastomeric copolymer of polybutylene terephthalate and glycols (Hytrel), rubber, and combination thereof. The belt joints should preferably be as straight as possible, to avoid increasing the profile of the belt, preferably a glued joint is used, most preferably a finger joint.

The belt conveyor may preferably be driven by a stepper motor or an electric motor with or without an additional gearbox. The belt speed can be controlled in the case of a stepper motor by a driver and/or potentiometer and in the case of an electric motor by a frequency converter. At the end of the belt conveyor (downstream of the separator), the remaining particles are preferably removed with a brush or rake or air, so that the particles do not contaminate the lower part of the device.

In some embodiments, the belt conveyor may be provided downstream of the liquid dispenser with a rake which, when the droplets pass, ensures that they are rotated and wrapped in solid particles.

In some embodiments, downstream of the liquid dispenser, the belt conveyor may be provided with a device for mechanical vibration in the horizontal and/or vertical direction, whereby the droplets in solid particles can be coated fully.

In some embodiments, a plate for collecting solid particles which have not been removed from the belt may be provided below the belt conveyor.

The separator separates the entire contents from the belt conveyor belt, for example by means of a rake or a brush. However, most solid particles and prepared liquid marbles have enough inertial force to separate from each other at the end of the belt, so a rake or brush may not be needed.

In some embodiments, the separator is provided with an inclined (sloping) stop for supporting particles. In this case, the contents of the belt first fall on the stop, where the coating of the liquid marbles may be finished. From the stop, the liquid marbles and other contents of the belt fall into other components of the separator.

The separator contains a device for separating the liquid marbles from the remaining (excess) solid particles. Such a device can be, for example, a vibrating screen or a system of vibrating screens. Usually, since both solid particles and liquid marbles have a relatively narrow size range, while their sizes are quite different, one vibrating screen is sufficient. However, if, for example, a mixture of liquid marbles is produced (which is possible in an embodiment with several solids dispensers and several liquid dispensers), it can then be separated by means of a system of vibrating screens.

The vibrating screens are preferably removable, which allows a screen to be replaced by another screen with a different mesh size.

Solid particles can be transferred from the separator back to the solids dispenser. The transport of these solid particles can be performed batchwise (e.g. manual exchange of containers) or continuously (by a conveyor separate from the belt conveyor for the production of liquid marbles). As a return conveyor, for example, another belt conveyor, a pneumatic conveyor, a screw conveyor, a vibrating conveyor or a combination thereof can be used.

The terms "upstream" or "before", and "downstream" or "behind" used in this description relate to the movement direction of the belt conveyor, i.e., from the solids dispenser to the separator.

Another object of the present invention is the use of the said device for producing liquid marbles.

Another object of the present invention is a method of producing liquid marbles using the device disclosed herein. The method comprises the steps of:

continuously applying a layer of solid particles to the moving belt conveyor by means of at least one solids dispenser, applying droplets of liquid to this layer by at least one liquid dispenser to at least partially coat the liquid droplets with the said solid particles, optionally rolling or rotating the said liquid droplets to be completely coated to form liquid marbles, transferring the said at least partially coated liquid droplets into a separator in which their coating by solid particles is completed (if needed) to form liquid marbles, separating the produced liquid marbles from the excess solid particles on the basis of their different sizes.

The whole liquid droplet is coated with solid particles either immediately after contact with the solid particles (e.g. by rolling or rotating the droplet, or due to a large difference in hydrophilic/hydrophobic properties of the liquid and the solid particles) or by means of components such as a stop behind the liquid dispenser or by means of a sloping stop located in the separator.

The process parameters affect the size and other properties of the prepared liquid marbles. In particular, the following parameters can be changed for the individual components: Belt: velocity. Solids dispenser: height and shape of the bed of solid particles, speed of the mechanical agitator. Liquid dispenser: dripping frequency, droplet diameter, drop height of the droplet (height of the liquid dispenser outlet above the belt). Separator: mesh size, number of screens.

BRIEF DESCRIPTION OF DRAWING

FIG. 1 shows a device described in Example 1.

EXAMPLES OF CARRYING OUT THE INVENTION

Example 1: Example of a Device

The device according to this embodiment is schematically shown in FIG. 1. The device comprises a belt conveyor 1 (in one specific embodiment the length of the belt is 1.5 m and the width is 0.155 m, made of polyester), which is provided with a solids dispenser 2 (bevelled block shape, in one specific embodiment having a volume of 4 l, made of polycarbonate) wherein the solids dispenser is filled with solid particles 3. From the solids dispenser, the solid particles are poured evenly onto the belt, the layer height is controlled and the uniformity or desired layer shape is ensured by a straight or perforated stop 4. In the direction of movement of the belt conveyor 1 (downstream), a liquid dispenser 5 (linear pump) is provided, with a dosing needle or a set of needles (one to six needles) and a reservoir 7 (heated block with a volume of 25 ml) containing liquid 6. At the end of the belt conveyor 1 a separator is arranged containing a sloping stop 9 for completing the coating of the liquid marbles. The separator further comprises a vibrating screen 8 for separating the formed liquid marbles from excess solid particles. The mesh size of the screen is 0.5 mm and the screen is made of stainless steel. The remaining (excess) solid particles 11 fall into a container 10 which, when filled, is dumped into the solids dispenser 2. The liquid marbles are then transferred for further processing or packaging, as indicated by arrow 13. Below the belt is a plate 12 collecting solid particles which have not been removed from the belt. This reduces contamination and dustiness. The liquid dispenser is height-adjustable within the range from 1 to 120 mm above the bed of solid particles. The spacing between the needles is 25 mm, and 15 mm from the edge of the belt. The belt velocity is controlled by a potentiometer in the range from 1 to 25 cm/s.

TABLE 1

Droplet size as dependent on liquid dispenser settings

| liquid | inner diameter of needle (mm) | flow rate (ml/min) | droplet generation frequency (Hz) | droplet size (mm) | | st. dev. (mm) | droplet volume (mm$^3$) |
|---|---|---|---|---|---|---|---|
| Rubitherm RT50 | 0.6 | 7.8 | 133 | 1.24 | ± | 0.02 | 1.00 |

TABLE 1-continued

| | | | Droplet size as dependent on liquid dispenser settings | | | | |
| liquid | inner diameter of needle (mm) | flow rate (ml/min) | droplet generation frequency (Hz) | droplet size (mm) | | st. dev. (mm) | droplet volume (mm$^3$) |
| --- | --- | --- | --- | --- | --- | --- | --- |
| Rubitherm RT50 | 0.72 | 1.01 | 2 | 2.34 | ± | 0.01 | 6.71 |
| 75% glycerol in water | 0.25 | 0.1 | 9.3 | 0.7 | ± | 0.01 | 0.18 |
| Rubitherm RT31 | 0.2 | 0.97 | 9.8 | 1.46 | ± | 0.04 | 1.65 |
| PEG 6000 | 0.27 | 1.01 | 4 | 1.88 | ± | 0.01 | 3.47 |

Example 2: Preparation of Liquid Marbles for Cell Cultivation

Aqueous solution of medium and cells was placed in a heated stirred liquid reservoir (37° C.), and a peristaltic pump delivered this aqueous solution to the liquid dispenser needle, by means of which individual droplets were formed. The volume of the thus prepared droplets ranged from 5 to 40 mm$^3$ in various embodiments of this experiment. PTFE (polytetrafluoroethylene) powder (particle size 35 μm) was used to coat the droplets. PTFE was dosed onto the belt from solids reservoir by means of solids disepnser located 3 to 5 mm above the belt, then the bed of solid particles was adjusted with a stop having trapezoidal ridges (the bottom line corresponds to the droplet diameter). The depth of the ridge was 1 to 3 mm and the liquid was dosed into the groove produced by the stop. A rake was placed downstream, in the middle of the length of the belt conveyor. The rake covered the droplet with solid particles, thus coating the entire surface of the droplet. A separator was placed just below the belt so that the powder and liquid marbles did not suffer any damage from the fall. After separating the solid particles by means of a vibrating screen, the individual liquid marbles were transferred to a 96-well plate and placed in a cell culture incubator.

Example 3: Preparation of Oil Liquid Marbles with a Dissolved Active Ingredient Various oils were used as liquids. The oils contained or did not contain an active ingredient, and had viscosities in the range of 1 to 550 mPa·s, density of 0.75 to 1.1 g/cm$^3$ and surface tension from 25 to 40 mN/m. Lactose (particle size 45 μm) was used as solid particles. Lactose was dispensed on the belt conveyor from a solids dispenser which was height-adjustable within the range of 4 to 12 mm. Dripping of the oil with or without an active ingredient was performed by means of linear pump with a syringe as a liquid dispenser. The droplet size ranged from 2 to 40 mm$^3$ in various embodiments of this experiment. Downstream from the liquid dispenser, in the middle of the length of the belt conveyor, a second solids dispenser with a solids reservoir was placed, which dispensed further lactose solid particles onto the belt, i.e. also onto the droplets, thus coating the droplets from above. A perforated rake was provided downstream from the second solids dispenser, which ensured agitation of the layer of solid particles between the droplets, thus rolling the droplets and completing the coating. Subsequently, the contents of the belt fell into a separator and onto a vibrating screen with a mesh size smaller than the liquid marbles but larger than 45 μm. The separated liquid marbles were transferred for further processing and the solids were poured back into the solids reservoir and reused.

Example 4: Preparation of Liquid Marbles from a Melt Mixture

A melt mixture with or without an active ingredient was heated a temperature which was 1 to 20° C. above the melting point of the mixture and homogenized, the melt viscosity was in the range of 5 to 1200 mPa·s, the density in the range of 0.7 to 1.3 g/cm$^3$ and the surface tension in the range of 25 to 45 mN/m. Solid particles of hydroxypropylmethylcellulose, lactose, methylcellulose with varying particle sizes (from 45 to 250 μm) were used to coat the liquid marbles. The solid particles were dispensed from a solids dispenser that was height-adjustable from 1 to 5 mm, and with a straight stop. Dosing of the melt mixture with or without active substance was performed by a heated dispenser with an outlet consisting of a set of needles with a diameter of 0.2 to 0.9 mm. The height-adjustable liquid dispenser allowed to control the temperature and the speed upon impact of the melt mixture onto the bed of solid particles, thus influencing the composition and the amount of particles in the coating. The higher the melt temperature above the melting point, the more solid particles formed the coating. The droplet size ranged from 0.5 to 40 mm$^3$ in various embodiments of this experiment. At the end of the belt, the mixture of liquid marbles and excess solid particles fell on a sloping stop, where the coating of the liquid marbles was completed. Subsequently, the liquid marbles were separated from the solid particles by a vibrating screen.

The invention claimed is:

1. A device for preparation of liquid marbles, characterized in that it comprises a belt conveyor (1) for carrying a layer of solid particles, said belt conveyor (1) being provided, successively in the direction of movement of the belt, with at least one solids dispenser (2) with a reservoir for solid particles, at least one liquid dispenser (5) with a reservoir (7) for liquid, and a separator for separating the prepared liquid marbles from solid particles; wherein the liquid dispenser comprises a pump; and wherein the pump is selected from a syringe pump, a pump with a syringe, a piston in a heated block, a pneumatic pump, a linear pump, a peristaltic pump, a centrifugal pump, a gear pump, a spindle pump, a single-channel or multiple-channel dispense solenoid valve, a diaphragm pump, a vane pump, a pneumatic pump, a hydrostatic pump, a screw pump, and a dosing valve.

2. The device according to claim 1, which further comprises means (4) for adjusting the height of the layer of solid particles, said means being located downstream of the solids dispenser (2).

3. The device according to claim 2, wherein the means for adjusting the height of the layer of solid particles is height-adjustable for setting heights of the layer of solid particles within the range of 1 to 20 mm.

4. The device according to claim 1, wherein the solids dispenser (2) is equipped with a mechanical agitator, a rotating disk with blades, or a vibrating wall, for preventing formation of an arching inside the solids dispenser.

5. The device according to claim 1, wherein the outlet of the liquid dispenser (5) is a hollow capillary with an inner diameter of 0.05 to 2.5 mm, or a set thereof, or a needle with an inner diameter of 0.1 mm to 0.9 mm with a straight or bevelled tip, or a set thereof.

6. The device according to claim 1, wherein the liquid dispenser (5) is further provided with a system for accurate and rapid droplet formation which vibrates regularly in contact with the dispenser.

7. The device according to claim 6, wherein the system for accurate and rapid droplet formation is selected from a diaphragm compressed by a regularly moving piston, a piezoelectric transducer acting on a liquid, a diaphragm compressed by a solenoid with a spring, a device producing an air flow along the dispenser needle, a device causing mechanical vibration of the needle in its longitudinal or transverse direction.

8. The device according to claim 1, wherein the liquid dispenser (5) is further provided with a system for regulating the temperature of the liquid to be dispensed.

9. The device according to claim 1, wherein the belt conveyor (1) is provided with a plurality of solids dispensers and/or with a plurality of liquid dispensers.

10. The device according to claim 1, wherein surface of the belt conveyor (1) belt is made of a material selected from teflonglass fabrics, teflon (polytetrafluoroethylene), silicone, metal, polyvinyl chloride, polyurethane, polyethylene, thermoplastic elastomeric copolymer of polybutylene terephthalate and glycols, rubber, and combination thereof.

11. The device according to claim 1, wherein the belt conveyor (1) is provided with a rake downstream of the liquid dispenser (5), said rake being configured for rolling or rotating of the droplets and completing their coating by solid particles.

12. The device according to claim 1, wherein the belt conveyor (1) is provided with a system for mechanical vibration of the belt located downstream of the liquid dispenser (5).

13. The device according to claim 1, wherein the separator is provided with a sloping stop (9) for carrying solid particles and for completing the coating of liquid marbles.

14. The device according to claim 1, wherein the separator comprises a vibrating screen (8) or a set of vibrating screens.

15. The device according to claim 14, wherein the vibrating screen(s) is/are removable.

16. The device according to claim 1, wherein the liquid dispenser (5) is height-adjustable.

17. A method of producing liquid marbles comprising the step of a device comprising:

a belt conveyor (1) for carrying a layer of solid particles, said belt conveyor (1) being provided, successively in the direction of movement of the belt, with at least one solids dispenser (2) with a reservoir for solid particles, at least one liquid dispenser (5) with a reservoir (7) for liquid, and a separator for separating the prepared liquid marbles from solid particles.

18. A method of producing liquid marbles, said method comprising the steps of:

providing a device comprising:

a belt conveyor (1) for carrying a layer of solid particles, said belt conveyor (1) being provided, successively in the direction of movement of the belt, with at least one solids dispenser (2) with a reservoir for solid particles, at least one liquid dispenser (5) with a reservoir (7) for liquid, and a separator for separating the prepared liquid marbles from solid particles, continuously applying a layer of solid particles to a moving belt conveyor (1) by means of at least one solids dispenser (2), applying droplets of liquid to this layer by at least one liquid dispenser (5) to at least partially coat the liquid droplets with the said solid particles, transferring the said at least partially coated liquid droplets into a separator in which their coating by solid particles is completed, if needed, to form liquid marbles, separating the produced liquid marbles from the excess solid particles on the basis of their different sizes.

19. The method of producing liquid marbles according to claim 18, further comprising rolling or rotating the said liquid droplets to be completely coated to form liquid marbles after applying droplets of liquid to this layer by at least one liquid dispenser (5) to at least partially coat the liquid droplets with the said solid particles.

* * * * *